United States Patent [19]
Reid et al.

[11] Patent Number: 6,051,552
[45] Date of Patent: Apr. 18, 2000

[54] LACTOBACILLUS THERAPIES

[75] Inventors: Gregor Reid, London; Andrew W. Bruce, Toronto, both of Canada; Henk J. Busscher, Thesinge; Henny C. Van der Mei, Groningen, both of Netherlands

[73] Assignee: Urex Biotech, Inc., London, Canada

[21] Appl. No.: 08/867,002

[22] Filed: May 30, 1997

Related U.S. Application Data

[60] Provisional application No. 60/018,689, May 30, 1996.

[51] Int. Cl.⁷ .................................................... A61K 35/74
[52] U.S. Cl. ..................... 514/8; 424/93.45; 424/234.1; 424/246.1; 435/170; 435/252.9; 435/317.1; 435/803; 435/820; 435/853; 435/854; 435/855; 435/856; 435/857
[58] Field of Search .............................. 514/8; 424/234.1, 424/246.1, 93.45; 435/170, 252.9, 317.1, 803, 820, 853, 854, 855, 856, 857

[56] References Cited

PUBLICATIONS

Hawthorne, Lesleyann et al. "The effect of protein and urine on uropathogen adhesion to polymer substrata," *Journal of Biomedical Materials Research*, 1990, 24, 1325–1332.

Reid, Gregor et al. "Adhesion of Lactobacilli to Polymer Surfaces in Vivo and in Vitro," *Microbial Ecology*, 1988, 16, 241–251.

Reid, Gregor et al. "Effect of Bacterial, Urine and Substratum Surface Tension Properties on Bacterial Adhesion to Biomaterials," *Biofouling*, 1991, 4, 171–176.

Reid, Gregor et al. "Microbial adhesion to biomaterials and infections of the urogenital tract," *Colloids and Surfaces B: Biointerfaces*, 1994, 2, 377–385.

Reid, Gregor et al. "Adhesion of lactobacilli to urinary catheters and diapers: Effect of surface properties," *Journal of Biomedical Materials Research*, 1994, 28 731–734.

Velraeds, Martine M.C. et al. "Interference of Lactobacilli and Lactobacillus Biosurfactants in Uropathogen Adhesion," *London, Ontario*, 1995, (live presentation of experiment results).

Velraeds, Martine M.C. et al. "Physicochemical and biochemical characterization of biosurfactants released by *Lactobacillus* strains," *Colloids and Surfaces B: Biointerfaces*, 1996, 8, 51–61.

Velraeds, Martine M.C. et al. "Inhibition of Initial Adhesion of Uropathogenic *Enteroccus faecalis* by Biosurfactants from *Lactobacillus* Isolates," *Applied and Environmental Microbiol.*, 1996, 62, 1958–1963.

*Primary Examiner*—Frederick Krass
*Attorney, Agent, or Firm*—Scully, Scott, Murphy & Presser

[57] ABSTRACT

The present invention is directed towards isolated lactobacillus biosurfactants and the process for producing same. The present invention is also directed to methods for preventing urogenital infection in mammals using the isolated lactobacillus biosurfactant. The present invention is further directed to methods of inhibiting microbial biofilm formation using the isolated lactobacillus biosurfactant to prevent the formation of bacterial biofilms, and to displace adherent biofilm-forming bacteria from surfaces.

22 Claims, 7 Drawing Sheets

LACTOBACILLUS THERAPIES

This application claims benefit of U.S. Provisional Application No. 60/018,689, filed May 30, 1996.

FIELD OF THE INVENTION

This invention relates to isolated biosurfactants and compositions containing same and methods employing said compositions for inhibiting adhesion of pathogens to biomaterials and biosurfaces, including epithelial tissues.

BACKGROUND OF THE INVENTION

Biomaterials have been applied extensively to the urogenital area of children and adults. For example, in 1992, approximately, 58 billion diapers, 74 billion tampons, and 16 million urinary catheters were used in North America alone. Of course, other biomaterials have also been used in other areas of the body as well as in the urogenital tract, such as stents, fibrous materials, diaphragms and the like. Unfortunately, the adhesion of bacteria to the surfaces of these biomaterials is one mechanism whereby pathogenic bacteria can form a nidus for infection. This is particularly important as there are many microorganisms in the urogenital tract to which these materials are exposed. For example, it has been shown that pathogenic bacteria bind to catheters, stents, tampons and fibrous material, leading to various urogenital infections. Therefore, there is a need to find some product that will reduce the risk of contracting infections and particularly urogenital infections.

It has been found that the urogenital tract of the healthy pre-menopausal female is dominated by lactobacilli, while the urogenital microflora of women suffering recurrences of urinary tract infection (UTI) is replaced almost entirely by uropathogens. In fact, facultative lactobacilli make up 50–90% of the aerobic vaginal microflora in premenopausal women, and are also abundant in the aerobic urethral flora of healthy women in the reproductive age, accounting for 38% of the aerobic flora. In vitro, animal and human studies have provided evidence that indigenous lactobacilli may protect the host against urinary tract infection.

Lactobacilli are able to interfere with uropathogenic bacteria through several mechanisms. Lactobacillus whole cells and cell wall fragments have been found to competitively exclude a range of uropathogens from adhering to uroepithelial cells (Chan, et al. (1985) *Infect. Immun.* 49:84–89; Reid, et al. (1987) *J. Urol.* 138:330–335). competitive exclusion of uropathogens from attaching to polymer and catheter surfaces by lactobacilli has also been demonstrated (Hawthorn, et al. (1990) *J. Biomed. Mater. Res.* 24:39–46; Reid and Tieszer (1993) Cells and Materials 3:171–176). Lactobacilli have also been shown to coaggregate with uropathogenic bacteria which, in combination with inhibitor production, may lead to elimination of the uropathogens from surfaces (Reid, et al. (1988) *Can. J. Microbiol.* 34:344–351). Lactobacilli are also known to produce a variety of metabolic by-products with antimicrobial activity, such as hydrogen peroxide, lactic acid, bacteriocins and bacteriocin-like substances. However, prior to the present invention, no one identified the biosurfactant substances produced by the lactobacilli that were responsible for inhibiting the adhesion of pathogenic and particularly uropathogenic bacteria. As described hereinbelow, the present inventors have identified that substance, isolated it, and discovered that this substance is important for the inhibitory effects described hereinabove.

Another major problem associated with biomaterial devices, especially catheters, is solved by the present invention. In relation to infection, the insertion of urethral catheters is perhaps best recognized for an association with not only urinary tract infections (UTI) but also bacteremia and sepsis. The inability to eradicate the infecting organisms appears, in many cases, to be due to failure of antimicrobial therapy to penetrate biofilms. Only by removing the device does the patient respond, temporarily in some cases, to drug treatment. The biofilm problem extends to many other areas including devices used in urological, nephrological, anesthetic, respiratory, cardiovascular, general surgical and orthopedic practice, for example.

A microbial biofilm is defined as an accumulation of microorganisms and their extracellular products to form a structured community usually on a surface. More recently, the term has been broadened to include biofilms at some distances away from a surface (e.g. in disease states such as prostatitis), and which exist in multiple as well as single layers of cells.

The formation of an infectious biofilm on biomaterials consists of several sequential steps, and includes the deposition of the infectious microorganisms, adhesion of the organisms, anchoring by exopolymer production and growth of the organisms.

Immediately after insertion of a device into the body, the material surface is contacted with body fluids, such as saliva, tear fluid, blood or urine, for example. Macromolecular components from these body fluids adsorb quickly onto the material surfaces to form a conditioning film, prior to the arrival of the first organisms. The deposition of such conditioning films has been demonstrated on surfaces such as urinary catheters and ureteral stents. The compositions of these conditioning films have not been specifically defined, but nitrogen, carbon, oxygen, calcium, sodium and phosphorous have been identified as composing elements by x-ray photoelectron-spectroscopy and energy dispersive x-ray analysis.

The importance of the conditioning film and the initially adhering microorganisms have long been underestimated. This is, in part, due to the fact that the subsequent growth of the organisms leads to the dense biofilms, eventually manifesting in a clinical problem. However, the important first link in the chain of events leading to the formation of mature biofilms involves the initially adhering organisms. Accordingly, this bond represents the link with the growing biofilm. If this linkage breaks, the formation of the biofilms is either prevented or the formed biofilm detaches, thereby aiding the eradication of infection.

Again, the present inventors have discovered a substance that inhibits biofilm formation. In fact, this substance is the same substance that inhibited the adhesion of the uropathogenic bacteria. This substance, which the present inventors have found is a biosurfactant of lactobacilli.

Biosurfactants are compounds released by various microorganisms including lactobacilli, with a distinct tendency to accumulate at interfaces, most notably the liquid-air interface. Biosurfactant production can be measured conventionally by axisymmetric drop shape analysis by profile (ADSA-P). Classes of biosurfactants can be distinguished, according to their chemical structure. The most extensively investigated biosurfactants are glycolipids, e.g. the rhamnolipids from *Pseudomonas aeruginosa*. Other types of biosurfactants are lipopeptides and protein-like substances, phospholipids, substituted fatty acids, and lipopolysaccharides. The biosurfactants produced by these bacteria have different functions. For example, dairy *Streptococcus thermophilus* can produce biosurfactants which cause their own desorption, and oral *Streptococcus mitas* strains produce biosurfactants with anti-adhesive properties against *Streptococcus mutans*.

Various physiological functions of biosurfactants have also been described. Biosurfactants can, inter alia, enable microorganisms to grow on water-immiscible compounds by lowering the surface tension at the phase boundary; biosurfactants can cause emulsification, and can stimulate adhesion of microbial cells to organic substrates.

Biosurfactants have advantages over synthetic surfactants and it is those advantages that make biosurfactants prime candidates for industrial and biomedical applications. Biosurfactants are biodegradable and those from lactobacilli are non-toxic to humans.

Heretofore, no one knew that lactobacilli produced biosurfactants. However, the present inventors have not only discovered that lactobacilli produce biosurfactants, but also have isolated same and have discovered that these isolated biosurfactants can be used to prevent biofilm formation and urogenital infections.

SUMMARY OF THE INVENTION

The present invention is directed towards isolated lactobacillus biosurfactants and the process for producing same. The present invention is also directed to methods for preventing urinary tract infections and vaginitis in mammals using the isolated lactobacillus biosurfactant. The present invention is further directed to methods for treating infections in mammals, both male and female, associated with the insertion of biological devices e.g. urogenital devices. The present invention is still further directed to methods of inhibiting microbial biofilm formation using the isolated Lactobacillus biosurfactant and to displacing adherent biofilm-forming bacteria from surfaces.

One aspect of the present invention is directed to an isolated Lactobacillus biosurfactant produced by harvesting Lactobacillus cells, washing and resuspending the cells in a buffer solution, subjecting the cells to conditions conducive to releasing biosurfactant, and separating the biosurfactant from said cells.

Another aspect of the present invention is directed to a method for preventing urogenital infection in mammals by coating a biosurface or biomaterial for insertion into a mammal with a uropathogenically inhibitory amount of a Lactobacillus biosurfactant.

A still further aspect of the present invention is directed to a method of inhibiting microbial biofilm formation comprising coating a biosurface or biomaterial for insertion into a mammal with a pathogenically inhibitory amount of a Lactobacillus biosurfactant.

Another aspect of the present invention is directed to a method of treating an adherent pathogenic biofilm comprising coating a biosurface or biomaterial for insertion into a mammal with a pathogenically inhibitory amount of a Lactobacillus biosurfactant.

Another aspect of the present invention is directed to a pharmaceutical formulation comprising a pathogenically inhibitory amount of a Lactobacillus biosurfactant.

DETAILED DESCRIPTION OF THE INVENTION

Figure 1:
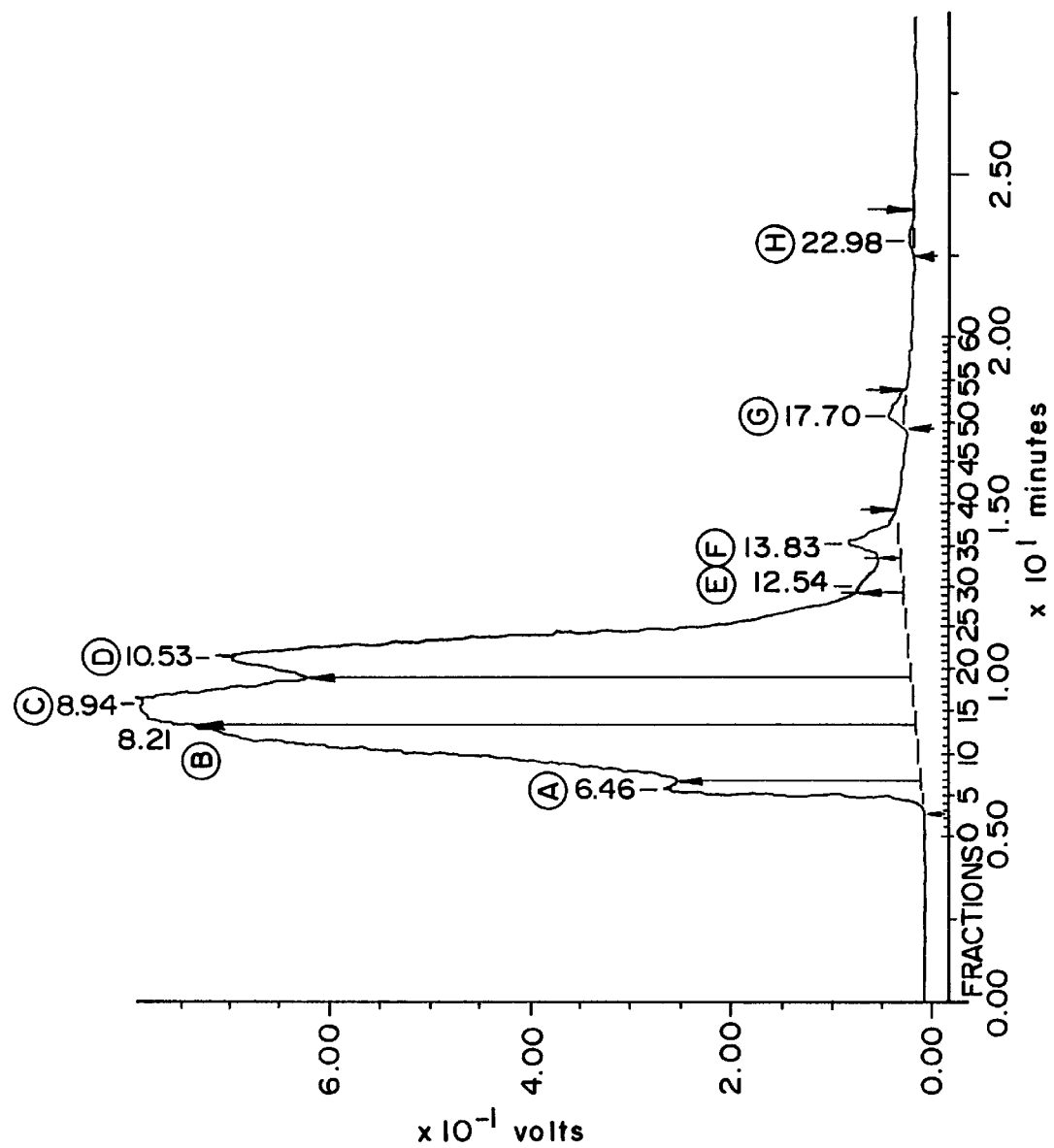
FIG. 1 shows High Performance Liquid Chromatography (HPLC) analysis of biosurfactant isolated from *L. acidophilus* RC-14.

One aspect of the present invention is directed to an isolated Lactobacillus biosurfactant. As defined by the present invention, a biosurfactant is a compound released by microorganisms with a distinct tendency to accumulate at interfaces, most notably the liquid-air interface.

Various strains of Lactobacillus have been used to prepare the biosurfactants of the present invention. They include *Lactobacillus acidophilus, L. casei, L. rhamnosus, L. plantarum* and *L. fermentum* and the like.

Preferred lactobacilli include: *Lactobacillus casei* var *rhamnosus* GR-1, *L. casei* 70, *L. casei* var *rhamnosus* 36, *L.* casei var *rhamnosus* 81, *L. casei* var *casei* ATCC 393 and *L. casei* var *rhamnosus* ATCC 7469. Other lactobacilli include *L. acidophilus* RC-14, *L. plantarum* RC-6, *L. plantarum* RC-20, *L. acidophilus* T-13, *L. fermentum* B-54, *L. fermentum* ATCC 23271, *L. fermentum* ATCC 14931, *L. acidophilus* ATCC 4356 and *L. plantarum* 14917. The lactobacilli are either aerobically or microaerophillically grown in a conventional culture medium. It is preferred that the latter group of lactobacilli be microaerophillically grown, while the former group is aerobically grown. Any growth medium typically used to culture bacteria can be utilized. However, it is preferred that the cultures are grown in MRS broth. As they are growing in the growth medium, the lactobacilli are producing the biosurfactants.

The biosurfactants were isolated from the lactobacilli by the following method: harvesting the Lactobacillus cells, washing and resuspending the cells in a buffer solution, subjecting the washed and resuspended cells to conditions conducive to release the biosurfactant; and separating the biosurfactant from the bacteria.

The Lactobacillus cells are harvested by conventional techniques, e.g. sonication, centrifugation and the like under conditions effective to harvest the cells. It is preferred that the lactobacilli are centrifuged under conditions sufficient to harvest the cells without any detrimental effects on the biosurfactant. Preferably, the lactobacilli are centrifuged at at least about 5,000 g and preferably from about 5,000 to about 20,000 g, although it is most preferred that the centrifugation takes place at about 10,000 g. In an even more preferred embodiment the Lactobacillus cells are centrifuged at about 10,000 g at effective harvesting temperatures, without denaturing or decomposing the biosurfactant. Preferably, the centrifugation is run at refrigerated temperatures (i.e., greater than 0° C. but less than about 15° C., and more preferably at about 4° C. to about 12° C. and most preferably at about 10° C. for sufficient time to harvest the cells. It is preferred that the centrifugation take place under the above conditions for at least 5 minutes and more preferably for about 5–10 minutes. In a more preferred embodiment, the lactobacilli are centrifuged at about 10,000 g at about 10° C.

The harvested cells are next washed and resuspended in conventional buffer. Preferably, the cells are washed with demineralized, deionized or distilled water. It is preferred that the pH of the buffer be about 6.0–8.0 and more preferably about 7.0. A preferred buffer is phosphate buffer solution (PBS).

The next step is the release of the biosurfactants from the suspended cells. This is accomplished by subjecting the suspended cells to conditions sufficient to release biosurfactant. This is accomplished by conventional techniques known in the art. In a preferred embodiment the washed and resuspended cells are subjected to mechanical stirring under conditions sufficient to release biosurfactant from the cells. Preferably, the cells are subjected to gentle agitation, such as from a mechanical stirring device, a stirring bar or by stirring of the buffer solution manually, utilizing a stirrer (e.g. glass stirrer), and the like. Preferably, the release of the biosurfactants is conducted at room temperature. Biosurfactant production can be monitored by the techniques described hereinbelow.

Finally, the biosurfactant is separated from the cells by conventional techniques. The preferred technique is by centrifugation and then separation of the supernatant which contains the biosurfactant from the solid, by techniques known in the art such as by decanting or filtering and the like. The separation of the supernatant may be facilitated with the use of a filter. Then, the biosurfactant is further purified by dialyzing the supernatant in a dialysis tube under sufficient conditions to substantially remove non-biosurfactant material, such as salts and other low molecular weight material that may be present. These non-biosurfactant materials diffuse out of the dialysis tube, leaving behind the biosurfactant produced in accordance with the present invention. Preferably, the dialysis tube has a MW cut-off at about 1,000 kDa to about 8,000 kDa, and preferably at about 8,000 kDa. It is preferred that the supernatant is dialyzed against demineralized water at 4° C. in a membrane tube. If stored for long periods of time the product may be subjected to freeze drying.

The biosurfactant can further be purified by conventional techniques known in the art, e.g. column chromatography, HPLC, preparative thin layer chromatography, electrophoresis and the like.

Biosurfactant production is conventionally measured in accordance with the present invention. In one aspect of the present invention, axisymmetric drop shape analysis by profile (ADSA-P) is performed to assess bacterial biosurfactant production in e.g. the mid-exponential growth phase and the stationary growth phase, using techniques known in the art. ADSA-P is used to calculate the liquid surface tension and the contact angle of an asymmetric droplet from its shape using the classical Laplace equation of capillarity, accordingly to Rotenberg, et al. (1983) *J. Coll. Interf. Sci.* 93:169–183, incorporated herein by reference. The amount of biosurfactant produced in a preferred technique is determined by its inhibition of the initial adhesion of Enterococcus in vitro.

A number of assays may be employed to examine the ability of Lactobacillus biosurfactants to inhibit the adhesion of microorganisms. In an embodiment of the present invention adhesion of, e.g. *Enterococcus faecalis* 1131 is measured in accordance with the present invention using a parallel plate flow chamber, using glass plates with and without an adsorbed biosurfactant layer. In another embodiment of the present invention, the ability of Lactobacillus biosurfactant to inhibit adhesion of uropathogenic microorganisms is measured using a polystyrene adhesion assay, as described in Example 4.

The present inventors have found that the biosurfactant isolated from the lactobacilli, after the dialysis step is extremely potent. In fact, the inventors have found that diluted Lactobacillus biosurfactant effectively reduces and effectively inhibits the initial deposition rate of and inhibits adhesion of e.g. Enterococcus in vitro. Therefore, preferred concentrations of the substances isolated after the dialysis step, in accordance with the present process, are diluted from about 5-fold to 50-fold. However, it is preferred that the Lactobacillus biosurfactant is diluted 10-fold. It has been found that a 10-fold diluted Lactobacillus biosurfactant inhibits adhesion of *Enterococcus faecalis* to e.g. glass, polystyrene and rubber for at least 4 hours.

Figure 2:
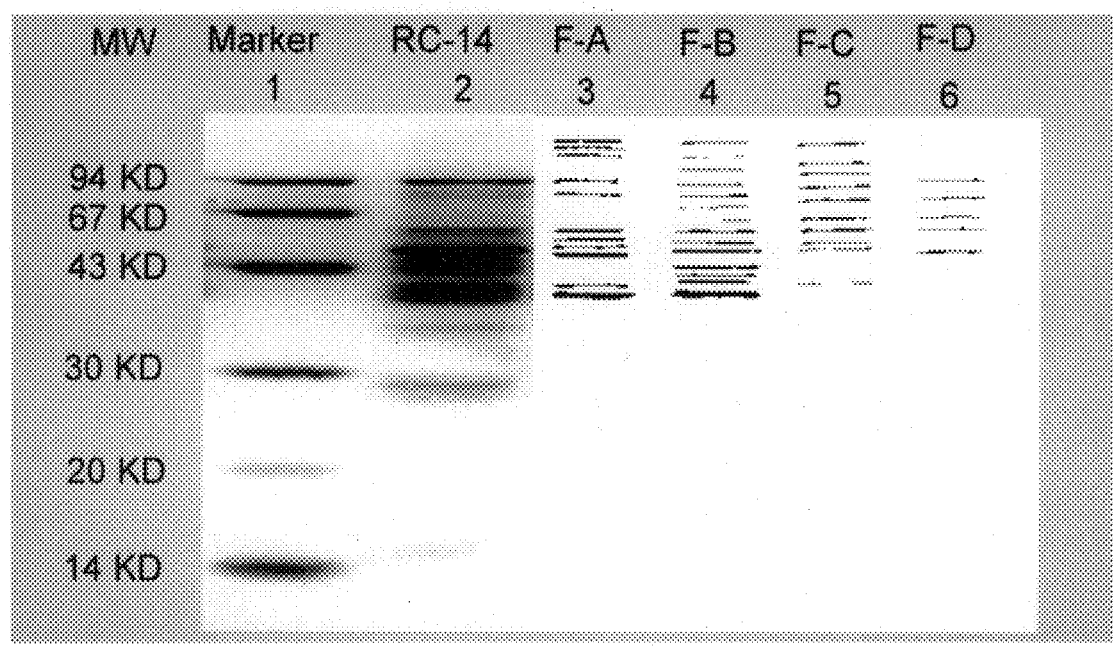
FIG. 2 is a SDS-polyacrylamide gel electrophoresis of Lactobacillus biosurfactant isolated from *L. acidophilus* RC-14.

The inventors have determined that the active substance produced by lactobacilli which inhibits adherence and colonization of pathogens on biological (e.g. urogenital) devices is protein-like. By "protein-like" is meant a biosurfactant having a predominantly proteinaceous character as conventionally determined by Fourier transform infrared spectroscopy (FTIR) and x-ray photoelectron spectroscopy (XPS), for example. The preferred isolated biosurfactants of the present invention are further characterized as having a molecular weight between about 8 kDa and 140 kDa (FIG. 2). Moreover, the isolated biosurfactants are comprised of most of the naturally occurring amino acids but predominantly contain alanine. A representative example of a biosurfactant isolated from two lactobacilli strains, e.g. L. casei var rhamnosus 36 and L. acidophilus RC14 is depicted in the following table (Table A).

pharmaceutical vehicles, such as carriers and adjuvants described in the literature of pharmaceuticals, cosmetics and related fields.

A topical cream may be conventionally prepared as a semi-solid emulsion of oil in water or water in oil comprising the Lactobacillus biosurfactants together with fatty alcohols, mineral oil or petrolatum and other typical pharmaceutical vehicles such as carriers, adjuvants, such as antioxidants, antiseptics and the like.

The biosurfactants are present in the various pharmaceutical formulations described hereinabove in pathogenically inhibitory amounts. "Pathogenically inhibitory", "effective amount" or "uropathogenically inhibiting" as used herein is defined as an amount of Lactobacillus biosurfactant sufficient to significantly inhibit the adhesion of uropathogens and other pathogens found outside the urinary tract (e.g.

TABLE A

Amino Acid Composition of Hydrolyzed Mid-Exponential and Stationary Phase Lactobacillus Biosurfactants

| Biosurfactant from | Amino Acid Composition (Mole %)[a] | | | | | | | | | | | | | | | |
|---|---|---|---|---|---|---|---|---|---|---|---|---|---|---|---|---|
| | Asx[b] | Glx[b] | Ser | His | Gly | Thr | Ala | Arg | Tyr | Val | Met | Phe | Ile | Leu | Lys | Pro |
| Mid-exponential Growth Phase | | | | | | | | | | | | | | | | |
| L. casei var rhamnosus 36 | 0.1 | 14 | 2.8 | 0.1 | 7.6 | 2.9 | 54 | 2.9 | 2.4 | 2.1 | 1.2 | 0.9 | 1.2 | 0.6 | 2.6 | 5.3 |
| L. acidophilus RC14 | 11 | 12 | 1.7 | 1.1 | 6.3 | 2.0 | 40 | 2.1 | 0.7 | 3.9 | 1.1 | 1.7 | 2.9 | 5.8 | 5.5 | 2.1 |
| Stationary Growth Phase | | | | | | | | | | | | | | | | |
| L. casei var rhamnosus 36 | 6.3 | 8.3 | 3.3 | 3.4 | 5.3 | 3.0 | 44 | 1.9 | 1.4 | 3.4 | 1.2 | 1.8 | 2.5 | 6.3 | 5.2 | 2.3 |
| L. acidophilus RC14 | 11 | 9.6 | 4.6 | 1.7 | 8.7 | 4.6 | 11 | 6.1 | 3.0 | 7.3 | 1.9 | 3.3 | 5.2 | 9.3 | 6.3 | 6.0 |

[a] Due to the analysis conditions, tryptophan and cysteine/cysteine cannot be quantified accurately.
[b] Asparagine and glutamine are deaminated into aspartic acid and glutamic acid, respectively.

The inventors have observed that biosurfactant production by lactobacilli is maximal for stationary phase cells grown under growth limiting conditions, e.g. limiting the nitrogen source.

The isolated biosurfactants of the present invention are administered in pharmaceutical compositions. The biosurfactants of this invention are preferentially administered topically, e.g. to the urinary epithelia and vaginal epithelia alone or prior to insertion or placement of a biodevice such as a diaper, tampon, urinary catheter, intravenous tube, dialysis tube, stent or diaphragm, for example.

It is generally preferred that the biosurfactants are administered topically or coat or partially coat that portion of the biosurface or biomaterial that is inserted or placed into the desired locus of the urinary or vaginal epithelia: Any common topical formulation such as a solution, suspension, gel, cream, ointment, or salve and the like may be used. Preparation of such topical formulations is well described in the art of pharmaceutical formulations as exemplified, for example, in Remington's pharmaceutical Science, Ed. 17, Mack Publishing Company, Easton, Pa. (1988).

In addition to the Lactobacillus biosurfactant described hereinabove, the compositions may additionally contain Staphylococcus aureus) but low enough to avoid serious side effects (at a reasonable benefit/risk ratio) within the scope of sound medical/scientific judgment. However, it is preferred that the formulation contains between 0.1 to 99 weight percent based on the total weight of the formulation for topical application. It is also preferred that the amount of the formulation of the present invention applied to a particular biosurface or biomaterial range from 0.001 $\mu$g to 100 $\mu$g/cm$^2$ relative to the area upon which the biosurfactant is applied.

It has been found that the biosurfactants produced by the present invention are effective in inhibiting adhesion of pathogenic, e.g. uropathogenic, bacteria. As indicated heretofore, the biomaterials act as a nidus for pathogenic infection. The pathogenic, e.g. uropathogenic, bacteria adhere to the surfaces. However, when the biosurfaces or biodevices are coated with effective amounts of the isolated biosurfactants of the present invention, their presence inhibits adherence of the uropathogenic bacteria. Accordingly, in another aspect of this. invention, the lactobacillus biosurfactant produced in accordance with the present invention inhibits or reduces the adherence and colonization of pathogens, e.g. uropathogens on biosurfaces and biomaterials, e.g. uroepithelia and catheter surfaces, for example. The Lactobacillus biosurfactant produced in accordance with the present invention significantly inhibits the adherence and colonization of e.g. *Enterococcus faecalis* to uroepithelial and vaginal epithelial cells.

In another aspect of the present invention, a method for preventing urogenital infection in mammals is provided which involves coating a biologically compatible device with a uropathogenically inhibitory amount of the lactobacillus biosurfactant and inserting the device into the urogenital tract. The uropathogenically inhibitory amount of lactobacillus biosurfactant coating is conventionally deposited on the outer surface of a biologically compatible device. The coating may also be conventionally applied to the inner surface of a device. The coating may be uniformly or non-uniformly deposited on the surface of a biologically compatible device. The biologically compatible device may be composed of polymers such as fluorinated ethylene propylene, sulfonated polystyrene, polystyrene, polyethyleneterephthalate silicone, polyurethane, polyvinylchloride silicone rubber, or glass, for example. The biodevice may be a catheter such as a urinary or peritoneal catheter, a diaphragm, a stent, an IUD or a diaper, an intravenous line, a peritoneal dialysis tube, an endotracheal tube, or an intravaginal, intrauterine, or intraurethral or intraureteral device, for example.

What has now been discovered, however, is that adsorbed biosurfactant produced by Lactobacillus species, in vitro, inhibited the initial adhesion of pathogenic microorganisms including *Escherichia coli, Enterococcus faecalis,* Klebsiella, *Proteus mirabilis, Providencia stuartii, Pseudomonas aeruginosa* and *Staphylococcus epidermidis*. It has further been discovered that the lactobacillus biosurfactants of the present invention inhibit the adhesion of pathogenic microorganisms including *Candida albicans, Escherichia coli, Enterococcus faecalis,* Klebsiella, *Proteus mirabilis, Providencia stuartii, Pseudomonas aeruginosa* and *Staphylococcus evidermidis* for a significant period of time, greater than about four hours.

For example, in accordance with the present invention, it has been found by the present inventors that *E. faecalis* adhesion to the *L. acidophilus* RC-14 biosurfactant layer is significantly delayed. The Lactobacillus biosurfactant produced in accordance with the present invention represents the first such substance which can resist microbial adhesion to biomaterials, including rubber, over a reasonable period of time (see Table B and Example 6).

TABLE B

| Strain | Biosurfactant layer (−/+) | Initial Disposition ($s^{-1}$ $cm^{-2}$) | Number After 4 h ($10^6$ $cm^{-2}$) |
| --- | --- | --- | --- |
| C. albicans | − | 101 | 1.13 |
| urine 1 | + | 58 | 1.11 |
| C. albicans | − | 76 | 0.79 |
| urine 2 | + | 38 | 0.74 |
| E. coli 67 | − | 197 | 2.41 |
|  | + | 17 | 0.52 |
| E. coli Hu734 | − | 17 | 1.10 |
|  | + | 0 | 0.18 |
| E. faecalis | − | 111 | 1.00 |
| 1131[a] | + | 0 | 0.04 |
| E. faecalis | − | 47 | 0.33 |
| 1396 | + | 0 | 0.02 |

TABLE B-continued

| Strain | Biosurfactant layer (−/+) | Initial Disposition ($s^{-1}$ $cm^{-2}$) | Number After 4 h ($10^6$ $cm^{-2}$) |
| --- | --- | --- | --- |
| E. faecalis 4b | − | 113 | 0.85 |
|  | + | 0 | 0.02 |
| Klebsiella 280 | − | 234 | 2.44 |
|  | + | 0 | 0.15 |
| Klebsiella a | − | 152 | 0.86 |
|  | + | 40 | 0.65 |
| P. mirabilis | − | 163 | 1.9 |
| 296[a] | + | 61 | 0.3 |
| P. mirabilis | − | 160 | 0.95[b] |
| 28cii[a] | + | 64 | 0.45[b] |
| P. stuartii | − | 288 | 8.86 |
| UHL 103 | + | 122 | 3.96 |
| P. stuartii | − | 34 | 0.31 |
| UHL 5292 | + | 7 | 0.18 |
| P. aeruginosa | − | 648 | 10.8 |
| AK1 | + | 420 | 9.50 |
| P. aeruginosa | − | 288 | 10.6 |
| ATCC 10145 | + | 365 | 6.07 |
| S. epidermidis | − | 95 | 1.8 |
| 3059[a] | + | 58 | 0.2 |
| S. epidermidis | − | 675 | 2.3 |
| 3081[a] | + | 110 | 0.4 |

[a]Triplicate experiments corresponding within 20%.
[b]Number of adhering bacteria after 2 h.

Another aspect of the present invention is directed to the use of pathogenically effective amounts of Lactobacillus biosurfactants to treat infections associated with the placement or insertion of biomaterials in contact with the urogenital tract, peritoneal space or blood stream, for example. The biosurfactant is applied topically in a pathogenically inhibiting amount to the infected epithelial tissue. The specific pathogenically effective amount of biosurfactant is conventionally determined by the skilled artisan. Alternatively, the biosurfactant is applied onto or into the biomaterial in effective amounts prior to insertion into the infected area. Upon insertion thereof, the biosurfactant forms a coating on the infected area, thereby inhibiting further colonization by pathogens. For example, upon insertion of a biomaterial, e.g. a peritoneal dialysis tube in the absence of a biosurfactant produced by the present invention, the tubing exit sites frequently become infected soon after insertion with the formation of biofilms. In accordance with the present invention, the use of the biosurfactant effectively inhibits the colonization of these bacteria. Without wishing to be bound, it is believed that Lactobacillus biosurfactants function by penetrating the biofilms, causing their displacement and ultimate breakdown thereby effectively treating the infected patient.

The biosurfactants of the present invention are also useful in the treatment of such diseases as vaginitis in females and urinary tract infections in males and females. As described hereinabove, the biosurfactant of the present invention is either applied topically to the affected area or onto the surface of a biomaterial for the treatment of those infections.

Still another aspect of the present invention is directed to the use of Lactobacillus biosurfactants to resist microbial biofilm formation, said biosurfactants being present in effective amounts to substantially prevent or reduce microbial biofilm formation.

A microbial biofilm is defined as an accumulation of microorganisms and their extracellular products to form a structured community on or near a surface. Microbial biofilms may exist as multiple or single layers of cells. It has been determined that the initiation of microbial biofilm formation is due to the adherence of pathogenic bacteria to the surfaces thereof. However, the present inventors have found that by coating the biosurfaces with a pathogenically effective amount of the isolated biosurfactant of the present invention, up to about 93% of the pathogenic bacteria are unable to adhere to the biosurfaces.

More specifically, the present inventors have now determined that the biosurfactant of the present invention acts to break the first link in the chain of events leading to the formation of a mature biofilm, i.e., inhibition of initially adhering organisms. Accordingly, the use of Lactobacillus biosurfactaats as an anti-adhesive for, e.g. catheters, has now been recognized in accordance with the present invention.

In still another aspect of the present invention biocompatible materials or surfaces are coated with a uropathogenically inhibitory amount of the biosurfactant produced by lactobacilli to inhibit the growth of uropathogenic bacterial biofilms upon insertion into a mammal. In a further aspect of the present invention, biosurfactant producing lactobacilli reduce the formation of biofilms and displace adherent biofilm-forming bacteria from biocompatible surfaces such as catheters, diapers, tampons, diaphragms, and stents for example.

The present invention can also be used for the prophylaxis and treatment of pathogenic infections resulting from the insertion of various biodevices into other parts of the body besides the urogenital area. For example, when IV tubing is used in other areas of the body such as arms, legs and hands, the device acts as a nidus for pathogenic infection. The application of the biosurfactant produced in accordance with the present invention onto these devices or into the area of insertion, prevents the colonization by of these pathogenic bacteria, or if already present prior to insertion, effectively prevents further spread of these bacteria and at the same time effectively eliminates the infection. In another embodiment of the present invention a biodevice, such as a peritoneal tube, may be coated with a uropathogenically inhibiting amount of biosurfactant to prevent adherence of pathogenic bacteria to the surface of said device for a reasonable period of time.

The amount of biosurfactant utilized may vary depending upon various factors, including but not limited to the specific utility, the site of the surface upon which the biosurfactant is ultimately going to be applied, whether the biosurfactant is being applied to a biosurface or onto or into a biomaterial, and the like. The efficacious amounts used for the various utilities are conventionally determined by the skilled artisan. As indicated hereinabove, the biosurfactants of the present invention are applied in pathogenically effective amounts. Preferentially, these amounts range from about 1 $\mu$g/ml to about 50 mg/ml, and more preferably from about 1 $\mu$g/ml to about 30 mg/ml.

As used herein the term "biomaterials" refers to synthetic materials that are inserted into e.g. the urogenital area of mammals. Examples include, catheters, IV lines, diaphragms, stents, tampons and the like. "Biomaterials" may also be inserted into other parts of the body, e.g. peritoneal cavity, trachea, arms and legs. Accordingly, the term "biomaterials" also includes peritoneal dialysis tubes and endotracheal tubes for example.

The term "biosurfaces" as used herein refers to cell surfaces such as epithelial cells or tissue(s) of a mammal.

The invention will now be illustrated by means of the following non-limiting examples.

EXAMPLE 1

In order to apply ADSA-P as a screening method for bacterial surfactant production, 100 $\mu$l of a bacterial suspension was placed on fluoro-ethylenepropylene (FEP)-Teflon and positioned in an enclosed chamber to prevent evaporation. The surface tension of the suspension droplet was calculated from its shape as a function of time for 2 hours at room temperature.

In accordance with the ADSA-P methodology bacterial suspension, e.g. lactobacilli, were grown in 20 ml of MRS broth. After 4 hours (mid-exponential phase growth) and 24 hours (stationary phase growth), about 10 ml of the culture was harvested by centrifugation at 10,000 g for 5 minutes at 10° C. and washed with PBS at pH 7.0. Bacteria were resuspended in PBS to a final concentration of about 5×10$^9$ cells per ml. Enterococci were prepared as described for lactobacilli but were instead grown in 10 ml of BHI broth. Biosurfactant producing strains were confirmed following a surface tension decrease greater than 8 mJ m$^{-2}$ after 2 hours, according to the methods of Van der Vegt, et al. (1991) *Appl. Microbiol. Biotechnol.* 35:766–770, incorporated herein by reference.

The liquid surface tension of the suspension droplets is plotted versus time in FIG. 4 of four Lactobacillus strains. *L. acidophilus* RC-14, *L. acidophilus* T-13, *L. casei* subsp. *rhamnosis* 81 and *L. fermentum* B-54, all produced biosurfactants after 4 hours and 24 hours of growth. 24-hour cultures demonstrated the largest and most rapid decrease in surface tension, accordingly, strains from the stationary growth phase demonstrated superior biosurfactant production (see Table 1). *E. faecalis* 1131 did not produce biosurfactants.

TABLE 1

| Strain | $-\Delta\gamma_{lv}$[a] (mJ m$^{-2}$) |
|---|---|
| *L. acidophilus* | |
| ATCC 4356 (type strain) | 27 ± 1 |
| RC14 | 26 ± 0 |
| T13 | 18 ± 3 |
| *L. casei* | |
| 70 | 21 ± 0 |
| *L. casei* subsp. *casei* | |
| ATCC 393 (type strain) | 12 ± 4 |
| *L. casei* subsp. *rhamnosus* | |
| ATCC 7469 (type strain) | 27 ± 1 |
| GR-1 | 19 ± 3 |
| 81 | 27 ± 1 |
| 36 | 19 ± 2 |

TABLE 1-continued

| Strain | $-\Delta\gamma_{lv}{}^a$ (mJ m$^{-2}$) |
|---|---|
| *L. fermentum* | |
| ATCC 14931 (type strain) | 27 ± 4 |
| ATCC 23271 | 20 ± 3 |
| B54 | 29 ± 1 |
| *L. plantarum* | |
| ATCC 14917 (type strain) | 24 ± 2 |
| RC6 | 23 ± 1 |
| RC20 | 26 ± 4 |
| *E. faecalis* 1131 | 4 ± 0 |

[a]$\Delta\gamma_{lv}$ was determined relative to the surface tension of PBS (68 mJ m$^{-2}$). Results are expressed as mean of duplicate experiments on separately grown cultures, with ± indicating the difference between the experiments.

EXAMPLE 2

High Performance Liquid Chromatography (HPLC)

Crude RC-14 biosurfactant was fractionated by HPLC-size exclusion chromatography. A Waters HPLC system was used with an ultraviolet (UV) detector at a wavelength of 280 nm. The mobile phase used was tris buffer (0.1 M Tris, 0.1 mM Na$_2$SO$_4$) with the pH adjusted to 7.2. The system was operated at a rate of 2 ml/min. by using 2 Waters I-125 columns. The standard molecular weights used were bovine serum albumin (BSA, 67 kDa), Ovalbumin (OVA, 43 kDa), trypsin inhibitor (20.1 kDa) and cytochrome C (13.5 kDa).

The protein content of the HPLC fractions was determined by pipetting diluted samples with the Bio-Rad dye reagent (1:4) in a 96-well microtiter plate as described by the Biorad protein assay method (Biorad Inc., Canada). Data was obtained by using a Titerken Multiskan Plus plate reader (Labsystems, Finland). at a wavelength of 595 nm. Standard protein concentrations used were obtained by doubling dilutions of a bovine serum albumin (BSA) solution in HBSS buffer (initial concentration of 80 µg/ml).

FIG. 1 shows results obtained for the HPLC analysis of the crude RC-14 biosurfactant. Results correspond to an injection of 9.4 mg of crude biosurfactant dissolved in 200 µl of tris buffer. A range of peaks is observed in the chromatogram and individual peaks were collected into fractions. For instance, peak A was collected into fraction A, by collecting the initial eluting fractions (Elution-fr #) 4 to 7, at a rate of 2 ml/min. The final volume of fraction A was 2.00 ml. All peaks were named subsequently (B, C, D, E, F, G and H) as they eluted from the column. Only peaks A to F were collected into fractions. The total protein content from fractions A to D was equal to 145.4 µg. A substantial amount of biosurfactant and especially over 90% by weight was found in Fractions A-C. Fraction A showed the highest amount of protein content of 21 µg/ml, as determined by the Bradford protein analysis, while fraction D contained the lowest protein content of 0.1 µg/ml. The protein content of fractions E and F was not determined. Table 2 shows summary of the results obtained by HPLC and the Bradford protein assay.

TABLE 2

Purification and Protein Analysis of the RC-14 Biosurfactant by HPLC-Size Exclusion Chromatography and the Bradford Protein Analysis

| Peak | R.T. (min.) | Elution fr # | Final Vol. (ml) | ~M.W. (kDa) | Protein (µg/ml) |
|---|---|---|---|---|---|
| A | 6.46 | 4–7 | 2.00 | 80 | 21.00 |
| B | 8.21 | 8–14 | 3.50 | 55 | 23.00 |
| C | 8.94 | 15–20 | 3.00 | 40 | 7.50 |
| D | 10.53 | 21–28 | 4.00 | 25 | 0.10 |
| E | 12.54 | 29–32 | 2.00 | 15 | ND |
| F | 13.83 | 33–37 | 2.50 | 10 | ND |

Samples were suspended in tris buffer (0.1 M tris, 0.1 M Na$_2$SO$_4$) with the pH adjusted to 7.2. R.T.=elution retention times; Elution fr#=initial fractions as they eluted from the column at a rate of 2 ml/min.; Peaks A to D, were collected into Final Fractions (A to D), Peaks E and F were collected into Fraction EF with a volume of 4.5 ml; Vol.=final fraction volume; M.W.=approximate molecular weights; ND=Protein character was not determined (Peaks E and F).

EXAMPLE 3

SDS-Page

HPLC biosurfactant fractions suspended in tris buffer were dialyzed against ddH$_2$O and freeze dried overnight. Freeze-dried HPLC fractions and the crude biosurfactant were suspended in an SDS dissociation buffer containing 50 mM tris-HCl (pH 7.2), 100 mM DTT, 2% SDS, 0.1% bromophenol blue, 10% glycerol. After heating samples for 5 minutes, 80–90 µl of each sample was applied to a 10% SDS-PAGE gel, followed by coomassie blue staining. Molecular Weight standards used were phosphorylase b (94 kDa), bovine serum albumin (67 kDa), ovalbumin (43 kDa)m carbonic anhydrase (30 kDa), soybean trypsin inhibitor (20.1 kDa), and a lactalbumin (14.4 kDa).

The crude RC-14 biosurfactant displayed protein bands ranging from 14 kDa to >94 kDa in size (FIG. 2, lane 2). HPLC purified fractions A, B, C and D showed protein bands of sizes >40 kDa. Fraction EF was not analyzed.

EXAMPLE 4

Polystyrene Adhesion Assay

The effects of the crude RC-14 biosurfactant and the purified HPLC fractions on the adhesion of uropathogenic *E. faecalis* 1131 to polymers, was studied in a polystyrene adhesion assay (Rosenberg, (1984) *FEMS Microbiol. Lett.* 25:41–45; Goldberg, et al. (1990) *Appl. Environ. Microbiol.* 56(6):1678, 1682; Harty and Knox (1990) *Microbiol. Ecol. in Health Dis.* 4:19–28; Klotz (1985) *Infect. Immun.* 50:97–101) and modified as described below. A 1.5 ml inoculum in BHI broth of a 24 hour subculture was used to inoculate 30 ml of BHI broth and incubated overnight (for 16 h). The stationary cells were harvested by centrifugation (3640 rpm, 10 min., 4° C.) in a GS-6 Beckman centrifuge with a GH-38 rotor (3750 rpm max., Beckman Instruments, Canada) and washed three times in phosphate buffered saline (PBS, 0.8% NaCl, 2.5 mM Na$_2$HPO$_4$, 6.8 mM NaH$_2$PO$_4$) with the pH adjusted to 7.0. Cells were pipetted up-and-down to break aggregates, subsequently counted in a Hemocytometer, and finally diluted to a concentration of 3×10*8 cells/ml in 8 ml of PBS.

A 200 µl inoculum of each biosurfactant solution was placed in 4 wells of a flat-bottom polystyrene microtiter plate (tissue culture treated polystyrene, Corning Glassworks, Corning, N.Y.) and incubated for biosurfactant adhesion for 18 hours, at 4° C., on a rotating platform (2.5 rpm). The 4 control wells were inoculated with the biosurfactant suspending buffer (tris buffer) alone. After incubation, the remaining solution was removed from the wells and 200 µl of the *E. faecalis* suspension in PBS were added to 2 of the 4 treated wells, while the remaining 2 wells were inoculated with PBS alone for 4 hours, at 4° C., on a rotating platform, 2.5 rpm. Unattached organisms were removed and wells were gently washed 3 times with PBS by pipetting. Subsequently, wells were stained with 200 µl of 1:1 dilute crystal violet for 15 minutes To remove excess dye, the plate was rinsed gently in a stream of running tap water, after which the plate was allowed to dry. Optical densities were determined in a Titerken Multiskan Plus plate reader (Labsystems, Finland) at 595 nm wavelength. The change in the average optical densities (OD) of the duplicate wells, relative to the control wells with PBS buffer, was determined. This change was an indirect measure of the number of adhered bacteria to the polystyrene well and was compared to the control wells pretreated without the biosurfactant (tris buffer alone). Results were expressed as percent adherence.

Figure 3:
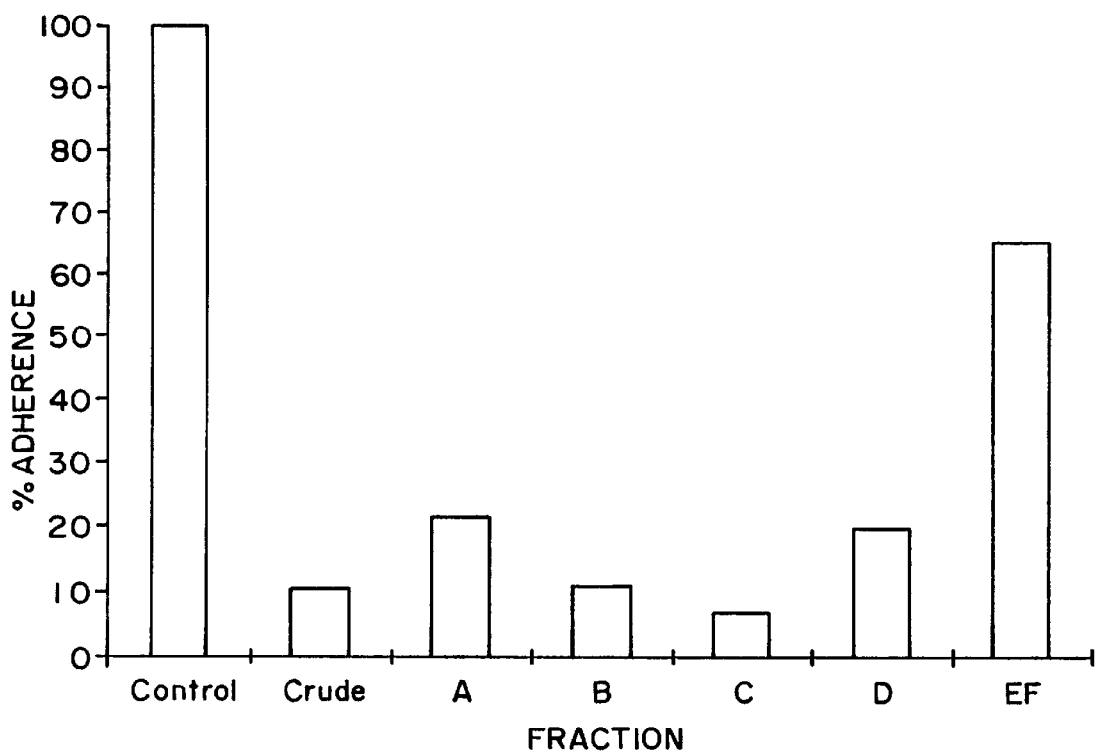
FIG. 3 shows the inhibition of adhesion of *E. faecalis* 1131 to tissue culture treated polystyrene after 4 hours by RC-14 biosurfactant and its purified fractions A, B, C, D and EF.
Figure 4A:
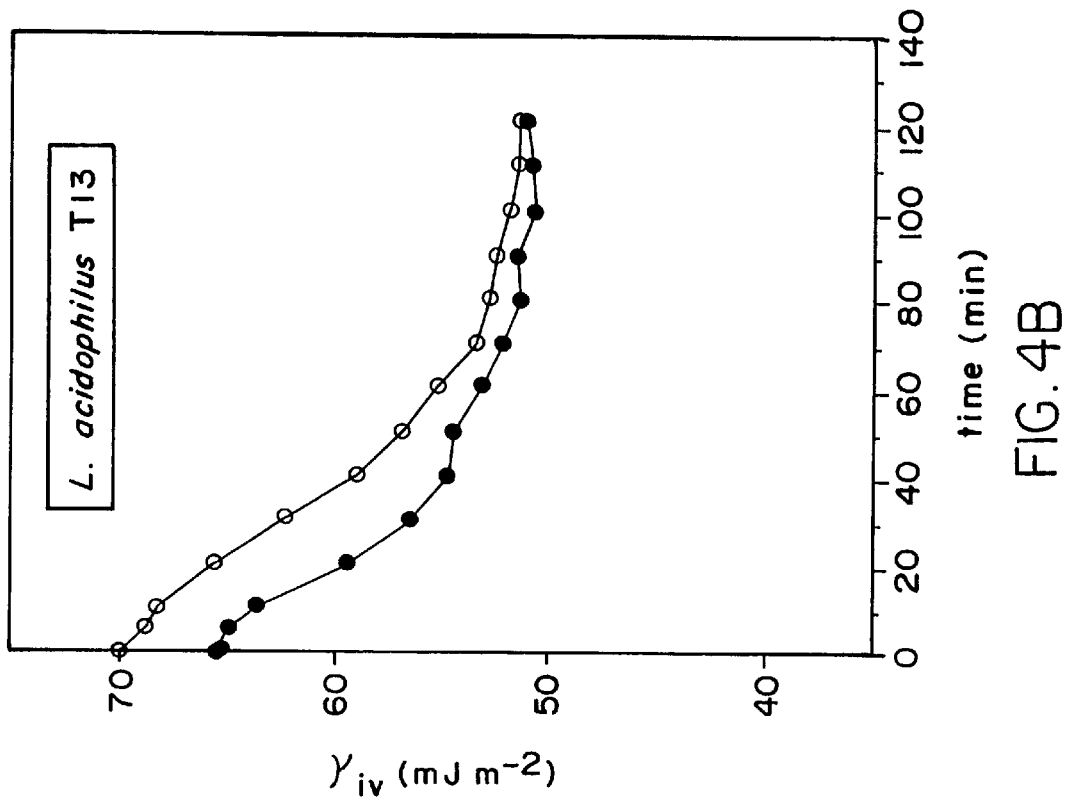
FIG. 4A plots the liquid surface tension of Lactobacillus acidophilus RC14 suspension droplets as a function of time by ADSA-P. Lactobacilli were harvested in their mid-exponential and stationary growth phase.
Figure 4B:
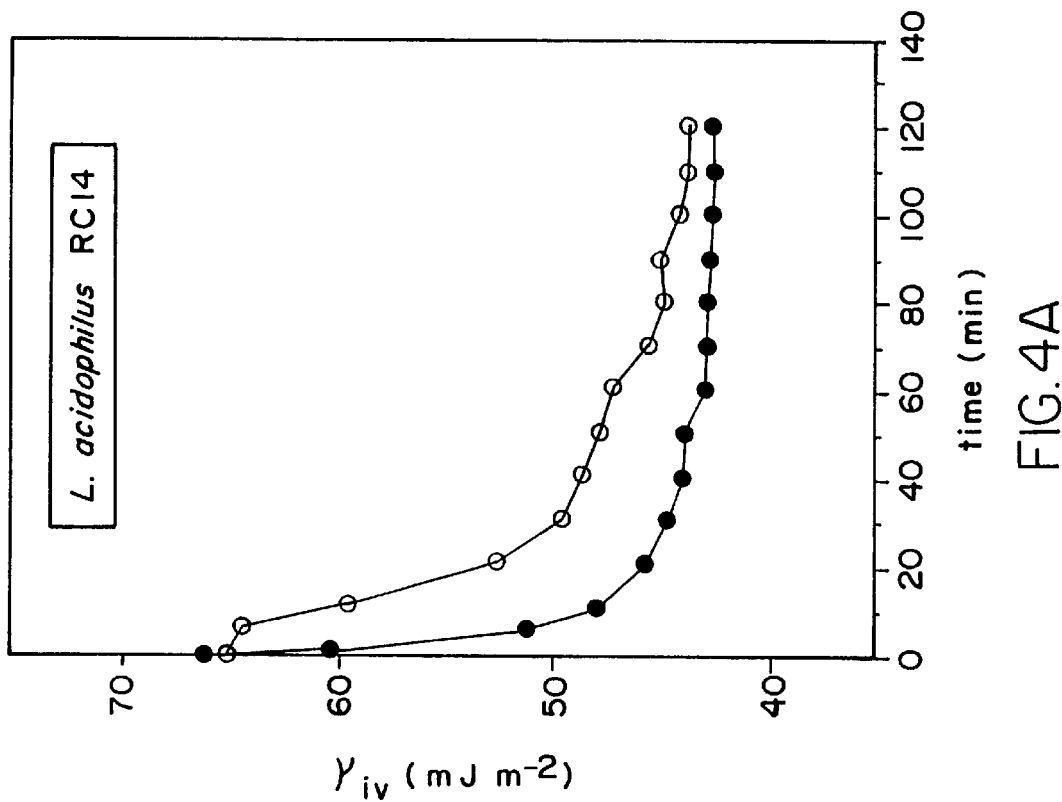
FIG. 4B plots the liquid surface tension of Lactobacillus acidophilus T13 suspension droplets as a function of time by ADSA-P. Lactobacilli were harvested in their mid-exponential and stationary growth phase.
Figure 4D:
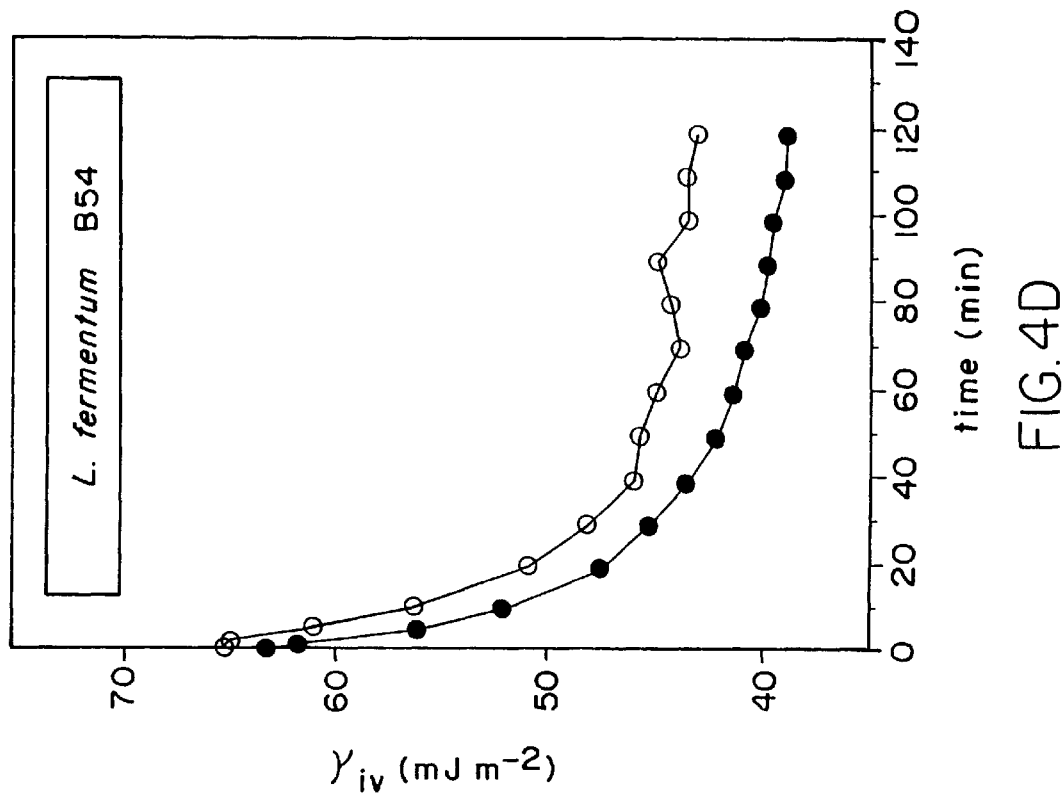
FIG. 4D plots the liquid surface tension of Lactobacillus fermentum B54 droplets as a function of time by ADSA-P. Lactobacilli were harvested in their mid-expotential and stationary growth phase.
Figure 4C:
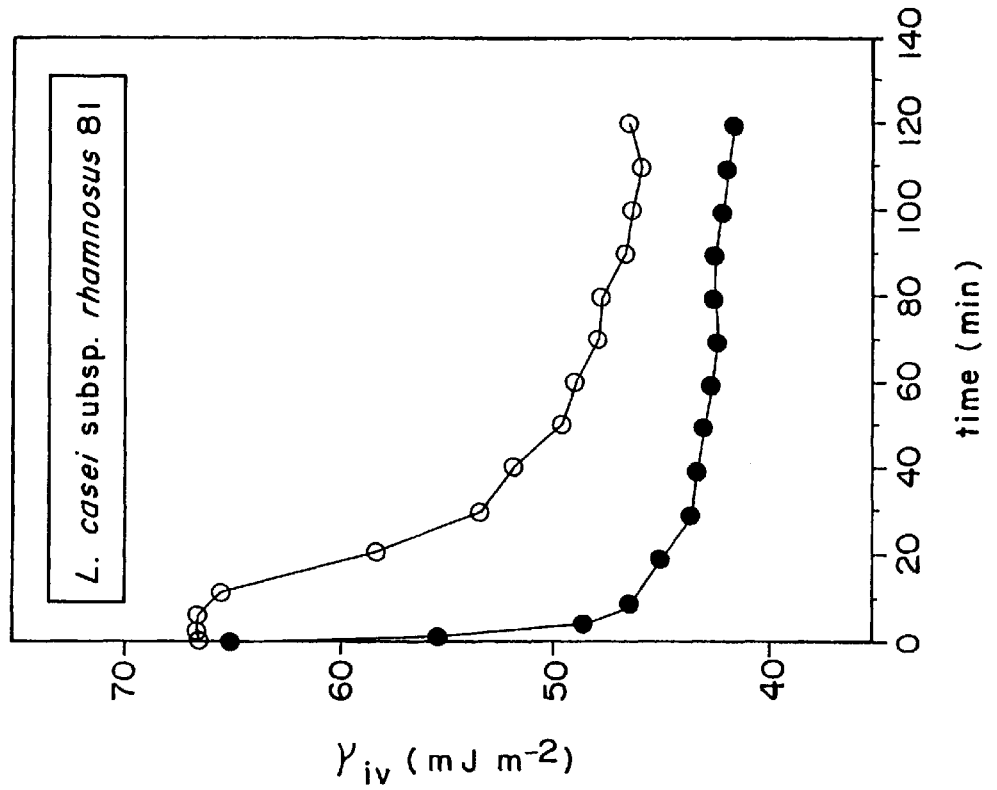
FIG. 4C plots the liquid surface tension of Lactobacillus casei subsp. rhamnosus B1 as a function of time by ADSA-P.
Figure 5:
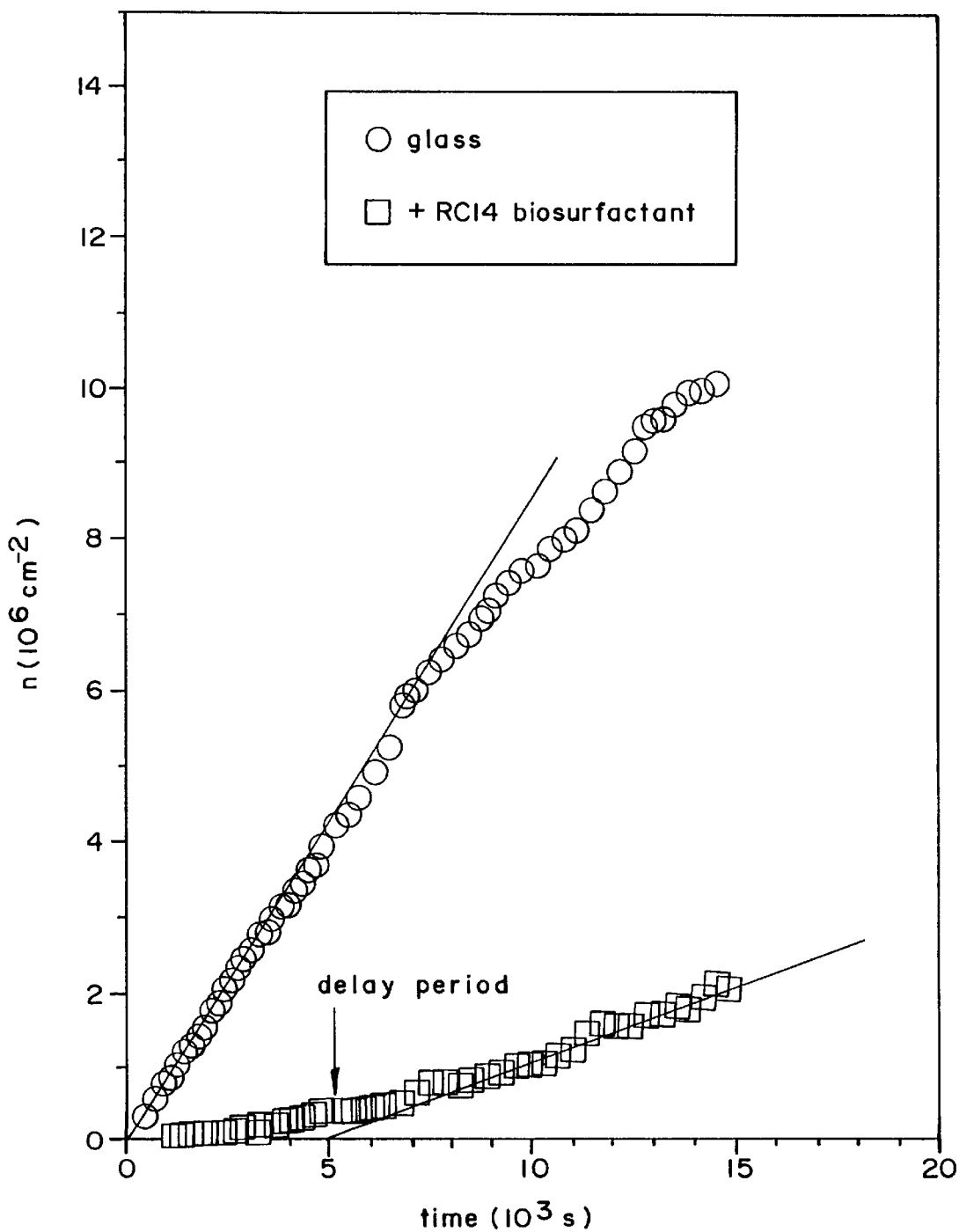
FIG. 5 shows the initial adhesion kinetics of a potent uropathogenic bacteria, *E. faecalis* 1131, in PBS to glass plotted against the adhesion of *E. faecalis* 1131 to glass with an adsorbed *L. acidophilus* biosurfactant layer studied in a parallel flow chamber.
Figure 6:
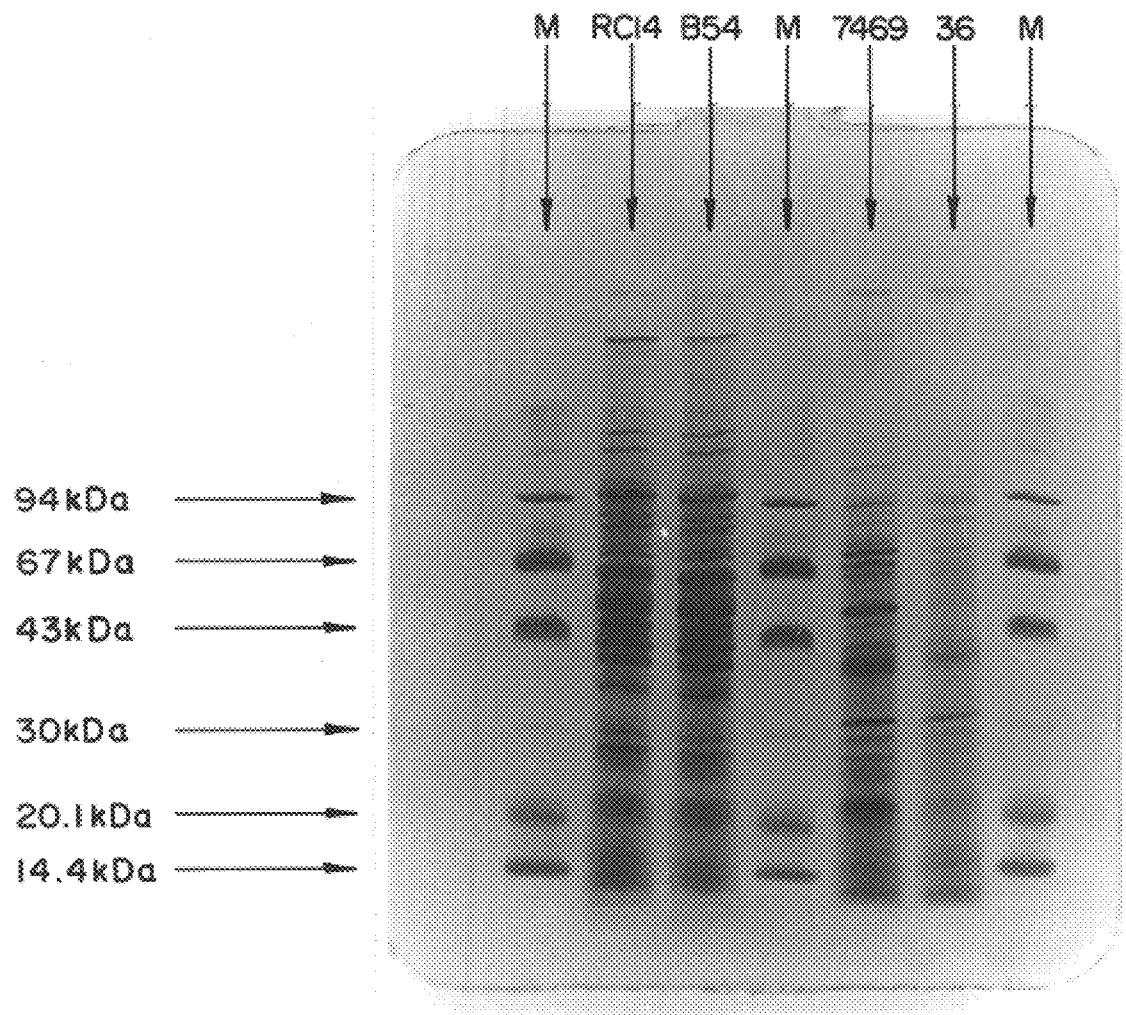
FIG. 6 is a SDS-polyacrylamide gel electrophoresis of Lactobacillus stationary phase biosurfactants: lane 1, molecular weight standards (M); lane 2, RC14; lane 3, B-54; lane 4, molecular weight standards (M); lane 5, ATCC 7469; lane 6, *L. casei* var *rhamnosus* 36; lane 7, molecular weight standards (M).

The crude RC-14 biosurfactant inhibited the adhesion of *E. faecalis* 1131 to treated polystyrene after 4 hours, by 89%. FIG. 3 illustrates the results of a single experiment done in duplicate. The purified fractions showed a range of activity that correlated the range of surface activity. Fraction C showed 93% inhibition of enterococcal adhesion, while fraction EF inhibited enterococcal adhesion by 35%. The crude RC-14 biosurfactant reduced enterococcal adhesion by 89%.

EXAMPLE 5

A parallel plate flow chamber was used to study deposition of *E. faecalis* 1131 to glass with and without an adsorbed biosurfactant layer. In order to obtain a laminar flow in the middle of the flow chamber, the depth and width of the inlet and outlet channels gradually decrease and increase, respectively. The flow chamber was mounted on the stage of a phase contrast microscope (Olympus BH-2) with a 40× objective having an ultralong working distance (Olympus ULWD-CD Plan 40 PL). A CCD camera (CCD-MX High Technology, Eindhoven, the Netherlands) was linked to an image analyzer (TEA image manager, Difa, Breda, the Netherlands), which was installed in a 667MHZ 486 personal computer. This system allowed the direct observation of bacterial adhesion over a field of view covering 0.011 mm$^2$.

Glass plates constituting the top and bottom plates of the chamber (5.5×3.8 cm), and two Teflon spacers (0.06 cm thickness) were cleaned ultrasonically in a 2% RES surfactant solution in water (Omnilabo International BV, the Netherlands) for 10 minutes, rinsed thoroughly with warm tap water, methanol, and demineralized water, and were finally secured into the flow chamber. Thus, prepared glass plates were completely wettable by water (zero contact angle). The flow chamber was filled with 10 ml freshly produced biosurfactant and left at room temperature for overnight adsorption. Subsequently, an *E. faecalis* suspension (3×10$^8$ cells ml$^{-1}$ in 250 ml PBS) was flowed through the system at room temperature. A pulse free flow (0.034 ml s$^{-1}$) was created by hydrostatic pressure, producing a constant shear rate of 15 s$^{-1}$, and the suspension was recirculated by using a peristaltic pump (Multiperpex 2115). Images were grabbed during the experiment and stored in the computer.

From the initial, linear increase of the number of adhering bacteria per unit area with time, the initial deposition rate $j_0$ was determined by a linear least-square fitting procedure. After 4 hours, the number of adhering bacteria was determined and the suspension was drained from the system, thus allowing an air-liquid interface to pass over the substratum (i.e., exposure to a high shear force). After draining, the flow was changed to the cell-free buffer and a final image was taken. The numbers of adhering bacteria in the postdraining and predraining images were compared, yielding the total number of bacteria retained after the passage of the air-liquid interface, as an indication for the strength of adhesion.

Initial adhesion kinetics of *E. faecalis* 1131 to glass and to glass coated with *L. acidophilus* RC-14 biosurfactant are presented in Table 3.

Biosurfactants from *L. acidophilus* RC-14 and *L. fermentum* B-54 inhibited the deposition rate of *E. faecalis* 1131 by 76% and 65% respectively (P<0.01, students t-test). Moreover, biosurfactants from *L. acidophilus* RC-14 and *L. fermentum* B-54 significantly inhibited the deposition rate of *E. faecalis* 1131 by 82% and 72% after 4 hours (P<0.01, students t-test).

TABLE 3

| Biosurfactant From | Delay Period (10$^3$s) | Initial Deposition Rate $j_0$(cm$^{-2}$s$^{-1}$) | Adhesion After 4 Hours (10$^6$cm$^{-2}$) |
| --- | --- | --- | --- |
| — | 0 | 889 ± 149 | 10.5 ± 1.8 |
| 36 | 0 | 739 ± 115 | 8.8 ± 1.6 |
| ATCC 7469 | 0 | 652 ± 30 | 9.0 ± 1.4 |
| B54 | 7.0 ± 0.6 | 313 ± 64 | 3.1 ± 0.3 |
| RC14 | 7.7 ± 0.2 | 209 ± 82 | 1.9 ± 0.7 |

[a]Results are expressed as mean ± SD of triplicate experiments, using separately grown cultures.

EXAMPLE 6

Silicone Rubber Adhesion Assay

Deposition of uropathogenic bacteria and yeasts to silicone rubber with an without an adsorbed layer of biosurfactant was studied in a parallel-plate flow chamber. Automated image analysis allowed in situ observation of bacterial and yeast cell adhesion over a microscopic field of view covering 0.011 mm$^2$ and 0.167 mm$^2$, respectively, as described previously Velraeds, et al. (1996) *Appl. Environ. Microbiol.* 62:1958–1963, incorporated herein by reference.

A parallel-plate flow chamber was filled with a biosurfactant solution of 1.0 mg ml$^{-1}$ in phosphate-buffered saline for overnight adsorption (18 h) at 4° C. Subsequently, the biosurfactant solution was drained from the flow chamber and bacterial or yeast suspension in urine ($3\times10^8$ cells $ml^{-1}$ and $3\times10^6$ cells $ml^{-1}$, respectively) was flowed through the system at room temperature. Experiments on the prepared biosurfactant layers and controls on clean silicone rubber were carried out simultaneously using the same batch of bacteria or yeasts. A pulse-free flow (0.034 ml $s^{-1}$) was created by hydrostatic pressure, and the suspension was recirculated by a Multiperpex 2115. peristaltic pump (Pharmacia LKB Biotechnology, Uppsala, Sweden), maintaining a constant shear rate of 15 $s^{-1}$. Based on the estimated daily urine production and internal catheter diameter, this shear rate is similar to that found at the luminal surface of a urinary catheter, and corresponds to a Reynolds number of 1, well within the laminar flow regime. During the experiment, images were obtained and stored in the computer.

From the initial, linear increase in the number of adhering bacteria or yeasts per unit area with time, the initial deposition rate was calculated by a linear, least-squares fitting procedure. After 4 h, the number of adhering microorganisms was determined and the suspension was drained from the system, allowing a liquid-air interface to pass over the substratum (i.e., exposure to a high shear force occurred). After draining, the system was filled with cell-free urine and a final image was taken. Based on the number of adhering bacteria or yeasts in the predraining and postdraining images, an average detachment after the passage of a liquid-air interface was calculated in percentages for all the uropathogenic strains tested as an indication of their strength of adhesion.

Table B shows the initial deposition rates and numbers of adhering bacteria or yeasts after 4 h for various uropathogens on clean silicone rubber (controls) and on silicone rubber with an adsorbed layer of the biosurfactant. From Table B, it can be concluded that for 11 out of the 15 uropathogenic bacteria tested, both the initial deposition rates and the numbers of adhering bacteria after 4 h were markedly reduced by the biosurfactant layers. This observed inhibition was particularly strong and consistent for *E. faecalis*, *E. coli* and *S epidermidis* species. In addition, the adhesion number of *P. aeruqinosa* ATCC 10145 after 4 h on silicone rubber with an adsorbed biosurfactant layer was also reduced by almost 50% when compared with the control.

Adsorbed biosurfactant layers caused a decrease in the initial deposition rates of *K. pneumonia* 3a, *P. stuartii* UHL 5292 and *P. aeruginosa* AK1 and had a minor effect on the numbers of adhering bacteria for 4 h, indicating that the inhibitory activity of the biosurfactant could be overcome by these bacteria after a certain time. Similarly, the initial deposition rates of the two *C. albicans* strains were inhibited by biosurfactant by approximately 50%, whereas the number of adhering yeast cells after 4 h were nearly equal to those of the controls.

Upon the passage of a liquid-air interface after 4 h of flow, the average detachment for all bacteria and yeasts was 69%±28% (SD) for control silicone rubber, and 47%±35% (SD) for silicone rubber with an adsorbed layer of biosurfactant. The tendency of the microorganisms to leave the substratum was higher for the control silicone rubber.

What is claimed is:

1. A Lactobacillus biosurfactant which has been isolated by (1) screening for biosurfactant production and (2) confirmation of biosurfactant production by measuring a surface tension decrease of a biosurfactant suspension greater than about 8 mJ $m^{-2}$, and wherein the biosurfactant is isolated by the method comprising:
   (a) harvesting Lactobacillus cells;
   (b) washing and resuspending said cells in a buffer solution;
   (c) subjecting said cells to conditions sufficient to release said biosurfactant; and
   (d) separating the biosurfactant from said cells.

2. The Lactobacillus biosurfactant of claim 1 wherein said screening for biosurfactant production is by axisymmetric drop shape analysis by profile (ADSA-P).

3. The biosurfactant of claim 1 wherein harvesting comprises centrifuging said cells under conditions sufficient to harvest said cells.

4. The biosurfactant of claim 3 wherein said cells are centrifuged at at least 5,000 g.

5. The biosurfactant of claim 3 wherein said cells are centrifuged at about 5,000 g to about 10,000 g at refrigerated temperatures.

6. The biosurfactant of claim 1 wherein step (c) comprises mechanically stirring said cells under conditions effective to release said biosurfactant from the cell.

7. The biosurfactant of claim 1 wherein separating comprises centrifuging the product of (c) under sufficient conditions to separate the cells from the supernatant containing the biosurfactant and decanting the supernatant.

8. The biosurfactant of claim 7 wherein the supernatant is additionally passed through a filter.

9. The biosurfactant of claim 1 wherein said method further comprises (e) dialyzing the biosurfactant produced in step (d).

10. The lactobacillus biosurfactant of claim 1 which inhibits adherence and colonization of *Candida albicans*, *Enterococcus faecalis*, *Escherichia coli*, *Enterococcus faecalis*, Klebsiella, *Proteus mirabilis*, *Providencia stuartii*, and/or *Pseudomonas aeruginosa*.

11. A method for reducing the occurrence of urogenital infection in mammals comprising coating that portion of a biomaterial that is inserted into the urogenital area of a mammal with a uropathogenically inhibitory effective amount of the biosurfactant produced according to claim 1 and inserting said coated biomaterial into the urogenital area of said mammal.

12. The method of claim 11 which reduces the occurrence of urogenital infection resulting from the formation of a biofilm.

13. A method for reducing the occurrence of urogenital infection in mammals comprising topically applying onto a urogenital biosurface, a uropathogenically inhibiting effective amount of the biosurfactant produced according to claim 1.

14. The method of claim 13 which reduces the occurrence of urogenital infection resulting from the formation of a biofilm.

15. The method of either claim 11 or 12 wherein said biomaterial comprises urinary catheters, diapers, intravenous lines, dialysis tubes, stents, peritoneal tubes, tampons, diaphragms or and endotracheal tubes.

16. The method of claim 12 or 14 wherein said biosurface is urinary or vaginal endothelia.

17. A pharmaceutical composition for topical application comprising a pathogenically inhibitory amount of the biosurfactant produced in accordance with claim 1 and a pharmaceutically acceptable vehicle therefor.

18. The pharmaceutical composition according to claim 17 which is in the form of an ointment, salve, cream or lotion.

19. A method of treating infections associated with the insertion of a biomaterial into mammals comprising coating said biomaterial prior to or simultaneous with insertion into a mammal with a pathogenically inhibitory effective amount of the biosurfactant produced according to claim 1.

20. A method of treating urogenital infections in mammals in need thereof comprising topically applying onto a urogenital biosurface, a uropathogenically inhibiting effective amount of the biosurfactant produced according to claim 1.

21. The method of claim 19 or 20 wherein the infections result from the formation of microbial biofilms.

22. The method according to claim 11 or 19 wherein said biomaterial is comprised of glass, rubber or polystyrene.

\* \* \* \* \*